United States Patent [19]

Merger et al.

[11] 4,294,971

[45] Oct. 13, 1981

[54] PREPARATION OF N-ARYLOXAZOLIDINE-2,4-DIONES

[75] Inventors: Franz Merger, Frankenthal; Friedrich Towae, Ludwigshafen, both of Fed. Rep. of Germany

[73] Assignee: BASF Aktiengesellschaft, Fed. Rep. of Germany

[21] Appl. No.: 127,759

[22] Filed: Mar. 6, 1980

[30] Foreign Application Priority Data

Apr. 4, 1979 [DE] Fed. Rep. of Germany ....... 2913522

[51] Int. Cl.³ ............................................ C07D 263/04
[52] U.S. Cl. .................................................. 548/226
[58] Field of Search ........................................ 548/226

[56] References Cited

U.S. PATENT DOCUMENTS

| | | | |
|---|---|---|---|
| 3,703,526 | 11/1972 | Sato et al. | 548/226 |
| 3,895,054 | 6/1975 | Zajacek et al. | |
| 3,956,360 | 5/1976 | Zajacek et al. | |
| 3,966,750 | 6/1976 | Mangold et al. | 548/226 |
| 3,979,427 | 9/1976 | Ottmann et al. | 260/453 PC |
| 3,995,049 | 11/1976 | Mangold et al. | 548/226 |

FOREIGN PATENT DOCUMENTS

| | | |
|---|---|---|
| 1811843 | 6/1973 | Fed. Rep. of Germany . |
| 2207576 | 8/1973 | Fed. Rep. of Germany . |
| 2343826 | 3/1974 | Fed. Rep. of Germany . |

*Primary Examiner*—Anton H. Sutto
*Attorney, Agent, or Firm*—Keil & Witherspoon

[57] ABSTRACT

N-Aryloxazolidine-2,4-diones are prepared by reacting a nitrobenzene with a 2-hydroxycarboxylic acid ester and carbon monoxide in the presence of selenium and a basic compound under super-atmospheric pressure and at an elevated temperature.

The N-aryloxazolidine-2,4-diones of the formula I, obtainable by the process of the invention are valuable active ingredients and starting materials for the preparation of crop protection agents, dyes and drugs.

10 Claims, No Drawings

PREPARATION OF N-ARYLOXAZOLIDINE-2,4-DIONES

The present invention relates to a novel process for the preparation of N-aryloxazolidine-2,4-diones by reacting a nitrobenzene with a 2-hydroxycarboxylic acid ester and carbon monoxide in the presence of selenium and a basic compound under superatmospheric pressure at an elevated temperature.

Oxazolidine-2,4-diones may be prepared by reacting an isocyanate with a 2-hydroxycarboxylic acid ester and cyclizing the product (cf. German Published Application DAS No. 1,811,843 and German Laid-Open Application DOS No. 2,207,576). The isocyanates required for this purpose are usually obtained from the corresponding amines by reaction with phosgene, and the amines, in their turn, are obtained from corresponding nitro compounds by reduction. The method of preparation is therefore involved, and necessitates the use of phosgene, which is toxic; accordingly, for safety reasons and to avoid pollution of the environment, expensive apparatus is required.

It has also been disclosed (German Laid-Open Application DOS No. 2,343,826) that urethanes may be prepared at elevated temperatures and under superatmospheric pressure from aromatic nitro compounds, organic compounds containing a hydroxyl group, and carbon monoxide, in the presence of selenium or sulfur. The only hydroxy compounds used in the Examples are methanol and ethanol. The starting materials mentioned individually in the description also do not contain any 2-hydroxycarboxylic acid esters.

We have found that an N-aryloxazolidine-2,4-dione of the formula

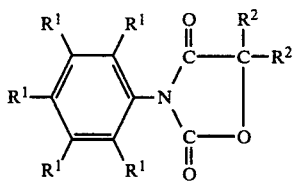

where the individual radicals $R^1$ and $R^2$ may be identical or different and each is hydrogen or an aliphatic, cycloaliphatic, araliphatic or aromatic radical, the two radicals $R^2$ may also together be a methylene radical and $R^1$ may also be halogen or $-X-R^3$, where $R^3$ is an aliphatic radical and X is oxygen or sulfur, is obtained in an advantageous manner if a nitrobenzene of the formula

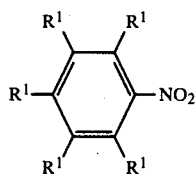

where $R^1$ has the above meaning, is reacted with a 2-hydroxycarboxylic acid ester of the formula

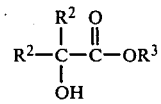

where $R^2$ and $R^3$ have the above meanings, and with carbon monoxide in the presence of selenium and a basic compound under superatmospheric pressure at an elevated temperature.

Where 3,5-dichloronitrobenzene and methyl vinyllactate are used, the reaction may be represented by the following equation:

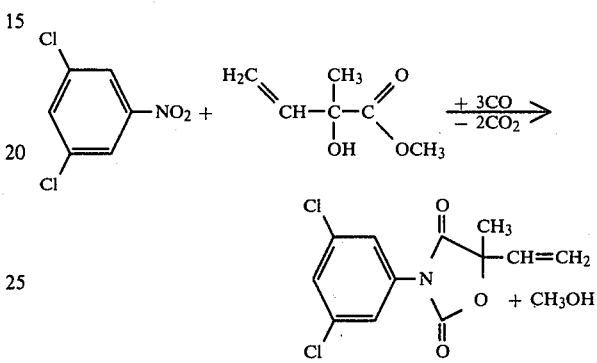

Compared to the conventional processes, the process according to the invention gives N-aryloxazolidine-2,4-diones more simply and economically, and in better yield. All these advantageous results are surprising in view of the prior art. The rapidly occurring formation of the end products I liberates an alcohol, which according to the disclosure of German Laid-Open Application DOS No. 2,343,826 should preferentially react with the aromatic nitro compound present to give the urethane of the alcohol. However, this urethane is not formed to a significant degree and instead the reaction takes place highly selectively to give the desired oxazolidine-2,4-dione I. Surprisingly, polyester formation by self-condensation of the 2-hydroxycarboxylic acid ester is also not observed under the reaction conditions.

The starting material II is reacted with the starting material III in stoichiometric amounts or using an excess of one over the other; advantageously, from 1 to 20, especially from 1.5 to 10, moles of starting material III are employed per mole of starting material II. Preferred starting materials II and III and accordingly preferred end products I are those where the individual radicals $R^1$ and $R^2$ are identical or different and each is hydrogen, alkyl of 1 to 7 carbon atoms, cycloalkyl of 5 to 7 carbon atoms, aralkyl or alkylaryl of 7 to 12 carbon atoms or phenyl, $R^2$ may also be alkenyl of 2 to 7 carbon atoms or alkoxymethyl of 2 to 7 carbon atoms, the two radicals $R^2$ together may also be methylene, and $R^1$ may also be chlorine, fluorine, bromine or $-X-R^3$, where $R^3$ is alkyl of 1 to 10, especially 1 to 7, carbon atoms and X is oxygen or sulfur. The above radicals may in addition be substituted by groups which are inert under the reaction conditions, for example alkyl or alkoxy each of 1 to 4 carbon atoms.

Examples of suitable nitrobenzenes II are nitrobenzene, 2-, 3- and 4-fluoronitrobenzene, 2-, 3- and 4-chloronitrobenzene, 2-, 3- and 4-bromonitrobenzene, 2,3-dichloronitrobenzene, 3,4-dichloronitrobenzene, 2,5-dichloronitrobenzene, 3,5-dichloronitrobenzene, 2,6-dichloronitrobenzene, 2,3,4-trichloronitrobenzene, 3,4,5-trichloronitrobenzene, 2,4,6-trichloronitrobenzene, 2,3,6-trichloronitrobenzene, 2,3,5-trichloronitrobenzene, 2-, 3- and 4-methoxynitrobenzene and 2-, 3- and 4-methylnitrobenzene, and corresponding nitrobenzenes which are substituted by ethyl, propyl, isopropyl, butyl, isobutyl, sec.-butyl, tert.-butyl, cyclohexyl, benzyl, phenyl, ethoxy, propoxy, isopropoxy, butoxy, isobutoxy, sec.-butoxy, tert.-butoxy, methylthio, ethylthio, propylthio, isopropylthio, butylthio, isobutylthio, sec.-butylthio or tert.-butylthio, the substituents being identical or different; particularly preferred compounds are 3,5-dichloronitrobenzene, 2-, 3- and 4-chloronitrobenzene, 2-, 3- and 4-bromonitrobenzene, 2-, 3- and 4-fluoronitrobenzene, all dichloronitrobenzenes, all trichloronitrobenzenes, 2-, 3- and 4-methoxynitrobenzene and 2-, 3- and 4-methylnitrobenzene.

Examples of suitable 2-hydroxycarboxylic acid esters are the methyl, ethyl, pentyl, propyl, isopropyl, butyl, sec.-butyl, tert.-butyl and isobutyl esters of hydroxyacetic acid, 2-hydroxypropionic acid, 2-hydroxybutyric acid, 2-hydroxyvaleric acid, 2-hydroxycaproic acid, 2-hydroxy-2-methylpropionic acid, 2-hydroxy-2-methylbutyric acid, 2-hydroxy-2-vinylpropionic acid and 2-hydroxy-2-phenylpropionic acid, corresponding esters of 2-hydroxyphenylacetic acid, 2-hydroxy-2-ethylphenylacetic acid and 2-hydroxy-2-vinylphenylacetic acid, and corresponding esters of the above acids which in addition to the 2-hydroxyl group also carry a methoxymethyl, ethoxymethyl, propoxymethyl, isopropoxymethyl, butoxymethyl, isobutoxymethyl or sec.-butoxymethyl group in the 2-position; the methyl, ethyl, propyl, isopropyl and isobutyl esters of 2-hydroxy-2-vinylpropionic acid, 2-hydroxy-2-methylpropionic acid and 2-hydroxy-2-methoxy-methylpropionic acid are preferred.

The reaction is in general carried out at from 80° to 250° C., preferably from 100° to 220° C., especially from 130° to 200° C., under superatmospheric pressure, preferably under from 50 to 1,000 bar, especially from 80 to 500 bar, advantageously from 80 to 300 bar, continuously or batchwise. Advantageously, solvents which are inert under the reaction conditions are used. Examples of suitable solvents are aromatic hydrocarbons, eg. toluene, o-, m- and p-xylene, methylnaphthalene, chlorobenzene, o-, p- and m-dichlorobenzene and o-, m- and p-chlorotoluene; ethers, eg. ethyl propyl ether, n-butyl ethyl ether, di-n-butyl ether, diisobutyl ether, diisoamyl ether, diisopropyl ether, anisole, phenetole, diethyl ether, ethylene glycol dimethyl ether, tetrahydrofuran and dioxane; and mixtures of the above. Advantageously, the solvent is used in an amount of from 400 to 10,000 percent by weight, preferably from 500 to 2,500 percent by weight, based on starting material II.

The reaction is carried out in the presence of a basic compound, advantageously used in an amount of from 1 to 30, preferably from 5 to 20, percent by weight based on starting material II. Preferred basic compounds are alkaline earth metal salts and alkali metal salts of organic carboxylic acids and of phosphoric acids, and in particular tertiary amines and cyclic amidines, as well as mixtures of the above. Suitable tertiary amines may be aliphatic, cycloaliphatic, araliphatic, aromatic or heterocyclic. Specific examples of suitable basic compounds are magnesium acetate, sodium formate, sodium acetate, sodium propionate, sodium butyrate, potassium formate, potassium acetate, potassium propionate, potassium butyrate, sodium phosphate, calcium phosphate, magnesium phosphate and potassium phosphate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, isoquinoline, α-picoline, β-picoline, γ-picoline, isoquinoline, pyrimidine, acridine, N,N,N',N'-tetramethylethylenediamine, N,N,N',N'-tetraethylethylenediamine, N,N,N',N'-tetramethyl-hexamethylenediamine, quinoxaline, quinazoline, N-propyldiisopropylamine, N,N-dimethylcyclohexylamine, 2,6-lutidine and 2,4-lutidine. Preferred compounds are pyridine, quinoline, isoquinoline, toluidine, p-dimethylaminopyridine, lithium acetate, sodium acetate, potassium acetate and especially 1,4-diaza-bicyclo-2,2,2-octane

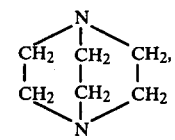

N-methylimidazole, 1,5-diaza-bicyclo[4,3,0]-non-5-ene

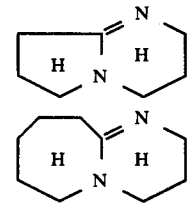

and 1,5-diaza-bicyclo-[5,4,0]-undec-5-ene

The selenium catalyst may contain selenium in a variety of modifications, for example amorphous, vitreous, hexagonal, monoclinic or cubic selenium, and advantageously selenium powder. A suitable material to use is pulverulent or amorphous or finely divided selenium as obtained, for example, on working up selenium-containing lead chamber sludge or on roasting selenium-containing sulfides.

Carbon monoxide prepared by conventional methods may be used, in the pure state and in most cases even in the crude state, for the process according to the invention. For example, crude carbon monoxide obtained by direct synthesis from coke and oxygen (Otto process), or by isolation from synthesis gases, generator gas, water-gas, coking gas, low temperature carbonization gas or gas mixtures resulting from the gasification of coal or coke, and worked up in the conventional manner, for example by means of a copper liquor wash, by the Cosorb method, by a liquid methane wash or by low temperature separation, may be used. The carbon monoxide may still contain impurities, such as carbon dioxide, oxygen, hydrogen, methane, nitrogen or argon, but advantageously the total amount of carbon dioxide, oxygen, methane and in particular hydrogen does not exceed 0.5 percent by weight of the carbon monoxide. The superatmospheric reaction pressure employed according to the invention is advantageously obtained as a result of the pressure of the carbon monoxide introduced, together with the autogenous pressure of the other reactants at the selected reaction temperature, but gases which are inert under the reaction conditions, for example nitrogen, may also be used to adjust the pressure. Advantageously, from 10 to 100, especially from 15 to 50, moles of carbon monoxide are employed per mole of starting material II.

The reaction may be carried out as follows: a mixture of starting materials II and III, carbon monoxide, catalyst, solvent and basic compound is kept for from 1 to 4 hours at the reaction temperature and the reaction pressure. The end product is then isolated from the mixture in the conventional manner, for example by filtration, distillation and recrystallization of the residue.

The known and the novel N-aryloxazolidine-2,4-diones of the formula I obtainable by the process of the invention are valuable active ingredients and starting materials for the preparation of crop protection agents, dyes and drugs. Regarding their use, reference may be made to the publications mentioned at the outset.

In the Examples which follow, parts are by weight, and bear the same relation to parts by volume as that of the kilogram to the liter.

EXAMPLE 1

35 parts of isobutyl 2-hydroxy-2-vinylpropionate, 9.6 parts of 3,5-dichloronitrobenzene, 1 part of selenium and 1 part of 1,4-diaza-bicyclo-[2,2,2]-octane

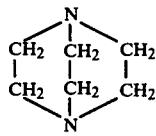

are introduced, together with 100 parts of chlorobenzene, into an autoclave of 400 parts capacity. The autoclave is flushed three times with nitrogen and carbon monoxide is then forced in to give an initial pressure of 150 bar. The reaction mixture is heated for 3 hours at 190° C. It is then cooled, the carbon monoxide is displaced by nitrogen and the reaction solution is discharged from the autoclave. After filtering the mixture, the solvent, excess isobutyl 2-hydroxy-2-vinylpropionate and unconverted 3,5-dichloronitrobenzene are distilled off and the residue is introduced into 25 parts of methanol. After filtration, 6.5 parts of N-(3',5'-dichlorophenyl)-5-methyl-5-vinyloxazolidine-2,4-dione (91% of theory), of melting point 108°–110° C., are obtained. The conversion of 3,5-dichloronitrobenzene is 50 percent.

EXAMPLE 2

Using the method described in Example 1, 9.6 parts of 3,5-dichloronitrobenzene are reacted with 56 parts of ethyl 2-hydroxy-2-methoxymethylpropionate, one part of selenium and one part of 1,4-diaza-bicyclo-[2,2,2]-octane in 100 parts of chlorobenzene for 3 hours at 190° C. under 200 bar initial pressure. After filtering the mixture, the solvent and excess ethyl 2-hydroxy-2-methoxymethylpropionate are distilled off and the residue is introduced into 25 parts of methanol. After filtration, 13.2 parts of N-(3',5'-dichlorophenyl)-5-methoxymethyl-5-methyloxazolidine-2,4-dione (87% of theory), melting point 105°–108° C., are obtained. The conversion of 3,5-dichloronitrobenzene is virtually quantitative.

We claim:

1. A process for the preparation of an N-aryloxazolidine-2,4-dione of the formula

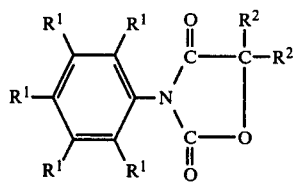

where the individual radicals $R^1$ and $R^2$ may be identical or different and each is hydrogen or an aliphatic, cycloaliphatic, araliphatic or aromatic radical, the two radicals $R^2$ may also together be a methylene radical and $R^1$ may also be halogen or $-X-R^3$, where $R^3$ is an aliphatic radical and X is oxygen or sulfur, wherein a nitrobenzene of the formula

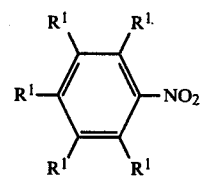

where $R^1$ has the above meaning, is reacted with a 2-hydroxycarboxylic acid ester of the formula

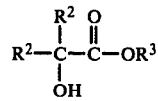

where $R^2$ and $R^3$ have the above meanings, and with carbon monoxide in the presence of selenium and a basic compound under superatmospheric pressure at an elevated temperature.

2. The process of claim 1, wherein the reaction is carried out with from 1 to 20 moles of starting material III per mole of starting material II.

3. The process of claim 1, wherein the reaction is carried out at from 80° to 250° C.

4. The process of claim 1, wherein the reaction is carried out at from 100° to 220° C.

5. The process of claim 1, wherein the reaction is carried out under from 50 to 1,000 bar.

6. The process of claim 1, wherein the reaction is carried out in the presence of from 400 to 10,000 percent by weight, based on starting material II, of a solvent which is inert under the reaction conditions.

7. The process of claim 1, wherein the reaction is carried out with from 1 to 30 percent by weight, based on starting material II, of a basic compound.

8. The process of claim 1, wherein the reaction is carried out with an alkaline earth metal salt or alkali metal salt of an organic carboxylic acid or of a phosphoric acid, or with a tertiary amine or cyclic amidine.

9. The process of claim 1, wherein the reaction is carried out with from 10 to 100 moles of carbon monoxide per mole of starting material II.

10. The process of claim 1 wherein the individual radicals $R^1$ and $R^2$ are identical or different and each is hydrogen, alkyl of 1 to 7 carbon atoms, cycloalkyl of 5 to 7 carbon atoms, aralkyl of alkylaryl of 7 to 12 carbon atoms or phenyl, $R^2$ may also be alkenyl of 2 to 7 carbon atoms or alkoxymethyl of 2 to 7 carbon atoms, the two radicals $R^2$ together may also be methylene, and $R^1$ may also be chlorine, fluorine, bromine or $—X—R^3$, where $R^3$ is alkyl of 1 to 10 carbon atoms, X is oxygen or sulfur and the above radicals may be substituted by alkyl or alkoxy each of 1 to 4 carbon atoms.

* * * * *